United States Patent
Kountotsis et al.

(10) Patent No.: US 9,114,064 B2
(45) Date of Patent: Aug. 25, 2015

(54) PACIFIER RECEIVING BREATH AND SALIVA SAMPLES FOR PROVIDING NUTRITIONAL INFORMATION

(76) Inventors: Theodosios Kountotsis, East Elmhurst, NY (US); Agjah Libohova, E. Setauket, NY (US)

(*) Notice: Subject to any disclaimer, the term of this patent is extended or adjusted under 35 U.S.C. 154(b) by 1153 days.

(21) Appl. No.: 13/068,004

(22) Filed: Apr. 29, 2011

(65) Prior Publication Data

US 2012/0277794 A1    Nov. 1, 2012

(51) Int. Cl.
*A61J 17/00* (2006.01)
*A61B 5/00* (2006.01)
*A61B 5/083* (2006.01)
*A61B 5/097* (2006.01)

(52) U.S. Cl.
CPC ............... *A61J 17/00* (2013.01); *A61B 5/6802* (2013.01); *A61J 17/001* (2015.05); *A61J 17/008* (2015.05); *A61B 5/083* (2013.01); *A61B 5/097* (2013.01); *A61B 2503/04* (2013.01); *A61J 2200/70* (2013.01)

(58) Field of Classification Search
CPC ........... A61J 9/00; G01N 27/00; G01N 21/00; G01N 33/497; A61B 5/08; A61B 5/083; A61B 5/0836; A61B 5/097; A61B 5/087
USPC .......... 600/532, 301, 344, 323; 606/234, 236; 340/573.1, 573.5
See application file for complete search history.

(56) References Cited

U.S. PATENT DOCUMENTS

| | | | |
|---|---|---|---|
| 5,705,735 A | 1/1998 | Acorn | |
| 5,830,235 A | 11/1998 | Standley | |
| 6,470,200 B2* | 10/2002 | Walker et al. | 600/344 |
| 7,333,020 B2* | 2/2008 | Cohen et al. | 340/573.1 |
| 2007/0232950 A1* | 10/2007 | West | 600/532 |
| 2009/0024004 A1 | 1/2009 | Yang | |
| 2009/0198275 A1 | 8/2009 | Godown et al. | |
| 2010/0004555 A1 | 1/2010 | Bazemore et al. | |
| 2010/0312133 A1 | 12/2010 | Bazemore et al. | |
| 2011/0054527 A1 | 3/2011 | Murphy Matro | |

FOREIGN PATENT DOCUMENTS

WO    WO2009132334 A1 * 10/2009 ................ A61J 9/00

* cited by examiner

*Primary Examiner* — Christine H Matthews
(74) *Attorney, Agent, or Firm* — Theodosios Kountotsis (57) ABSTRACT

A pacifier is presented including a nipple configured to receive a plurality of breath and saliva samples from a user, a base portion configured for attachment to the nipple, and an output mechanism attached to the base portion and configured for displaying different nutritional information values. The output mechanism may include one or more removable strips. The plurality of breath and saliva samples received from the user via the nipple are analyzed for nutritional information, preferably, continuously and in real-time, and the nutritional information includes at least one of carbohydrates, fats, minerals, protein, fiber, vitamins, water, salt, sugar, sodium, antioxidants, and phytochemicals.

19 Claims, 6 Drawing Sheets

PACIFIER RECEIVING BREATH AND SALIVA SAMPLES FOR PROVIDING NUTRITIONAL INFORMATION

BACKGROUND

1. Field of the Related Art

The present disclosure relates to pacifiers, and more particularly, but not exclusively, to a pacifier having breath and saliva collection, analysis, storage, and output capabilities for providing at least nutritional information of a user, preferably continuously and in real-time.

2. Description of the Related Art

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions. Therefore, unless otherwise indicated herein, what is described in this section is not prior art to the description and claims in this application and is not admitted to be prior art by inclusion in this section.

Infant pacifiers are known and available. Common among infant pacifiers are elements including a nipple on which an infant may suck, a base upon which the nipple is attached to prevent the infant from choking or otherwise ingesting the nipple, and often times a handle or similar structure to allow the infant or an adult to grip and place the pacifier.

Pacifiers have been used by parents to calm and satisfy infants between meals, thus freeing them to perform the many other necessary tasks in the caring for the infant. Pacifiers are also used to calm infants when they are stressed or just to keep them occupied between meals. However, it is difficult to predict when an infant/child needs nourishment (e.g., is hungry or thirsty) and it is difficult to determine whether an infant/child has received the appropriate amounts of nourishment. Thus, parents are left in limbo when an infant/child cries and resort to guessing what the infant/child requires with regard to nourishment. Additionally, after feeding has taken place, the parents are not aware of whether the infant/child has received the appropriate amounts of nutrients required for proper growth (e.g., to prevent overfeeding or underfeeding).

Therefore, it is clear that substantial room exists for affecting an advancement in the pacifier art, which overcomes these shortcomings in a practical and efficient manner.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides for a pacifier assembly including a nipple having a lower portion and an upper portion, the upper portion configured to receive breath samples from a user; a base portion attached to the lower portion of the nipple; and a grip portion attached to the base portion; wherein the breath samples received from the user via the nipple are analyzed for nutritional information.

The nutritional information includes at least one of carbohydrates, fats, minerals, protein, fiber, vitamins, water, salt, sugar, sodium, antioxidants, and phytochemicals.

In one exemplary embodiment, the breath samples are collected continuously and in real-time.

In yet another exemplary embodiment, the nipple includes one or more sensors positioned thereon or embedded therein. The one or more sensors measure at least one of pressure, humidity, temperature, oxygen levels, oxygen inhaled, oxygen exhaled, and carbon dioxide consumed. The one or more sensors are configured to compute at least one of: (i) a difference between the oxygen inhaled and the oxygen exhaled, (ii) the oxygen levels of each of the breath samples received from the user via the nipple, and (iii) a respiratory quotient.

The base portion includes one or more removable strips configured to display nutritional information values based on the breath samples received from the user via the nipple. The one or more removable strips include a plurality of areas each configured to indicate different nutritional information values. The nutritional information values are indicated via different indicia, colors or patterns.

In yet another exemplary embodiment, the nutritional information is wirelessly transmitted to an electronic device. In another exemplary embodiment, the nipple includes a filtering mechanism or air sanitizing mechanism actuated by a sucking motion of the user. In yet another exemplary embodiment, the pacifier assembly may include a sound emitting mechanism configured to emit sounds based on the breath samples received from the user via the nipple.

A storage unit may be provided for storing the breath samples received from the user via the nipple. Additionally, a processing unit may be provided for processing historical data associated with the breath samples received from the user and creating a user breath profile.

In yet another exemplary embodiment, the nipple is a hollow structure configured for receiving, storing, and analyzing saliva in conjunction with the breath samples of the user for providing the nutritional information.

The present disclosure also provides a method of providing nutritional information. The method includes the steps of inserting a pacifier assembly into an oral cavity of a user, the pacifier assembly including: a nipple having a lower portion and an upper portion; a base portion attached to the lower portion of the nipple; and a grip portion attached to the base portion; receiving breath samples from the user via the nipple; and analyzing the breath samples for extracting the nutritional information; wherein the nutritional information includes at least one of carbohydrates, fats, minerals, protein, fiber, vitamins, water, salt, sugar, sodium, antioxidants, and phytochemicals.

The present disclosure further provides for a pacifier including a nipple configured to receive a plurality of breath and saliva samples from a user; a base portion configured for attachment to the nipple; and an output mechanism attached to the base portion and configured for displaying different nutritional information values, the output mechanism having one or more removable strips; wherein the plurality of breath and saliva samples received from the user via the nipple are analyzed for nutritional information continuously and in real-time, the nutritional information including at least one of carbohydrates, fats, minerals, protein, fiber, vitamins, water, salt, sugar, sodium, antioxidants, and phytochemicals.

The present disclosure further provides for a nutritional information device may be presented including an orifice configured to receive a plurality of breath samples from a user, a base member configured for attachment to the orifice and an output mechanism attached to the base member and configured for displaying different nutritional information values based on the plurality of breath samples received, the output mechanism having one or more removable strips. The plurality of breath samples received from the user via the orifice are analyzed for nutritional information, the nutritional information including at least one of carbohydrates, fats, minerals, protein, fiber, vitamins, water, salt, sugar, sodium, antioxidants, and phytochemicals.

The present disclosure also provides a method for manufacturing a pacifier having breath and saliva collecting, analyzing, and storing capabilities, the method including the steps of forming/constructing/fabricating a nipple having a lower portion and an upper portion, the upper portion configured to receive breath samples from a user; forming/constructing/fabricating a base portion attached to the lower portion of the nipple; and forming/constructing/fabricating a grip portion attached to the base portion; wherein the breath samples received from the user via the nipple are analyzed for nutritional information.

The present disclosure also provides a method for manufacturing a pacifier having breath and saliva collecting, analyzing, and storing capabilities, the method including forming/constructing/fabricating a nipple configured to receive a plurality of breath and saliva samples from a user; forming/constructing/fabricating a base portion configured for attachment to the nipple; and forming/constructing/fabricating an output mechanism attached to the base portion and configured for displaying different nutritional information values, the output mechanism having one or more removable strips; wherein the plurality of breath and saliva samples received from the user via the nipple are analyzed for nutritional information continuously and in real-time, the nutritional information including at least one of carbohydrates, fats, minerals, protein, fiber, vitamins, water, salt, sugar, sodium, antioxidants, and phytochemicals.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the present disclosure will be described herein below with reference to the figures wherein.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Accordingly, while the present disclosure is susceptible to various modifications and alternative forms, specific embodiments thereof are shown by way of example in the drawings and will herein be described in detail. It should be understood, however, that there is no intent to limit the present disclosure to the particular forms disclosed, but on the contrary, the present disclosure is intended to cover all modifications, equivalents, and alternatives falling within the spirit and scope of the present disclosure as defined by the claims. Like numbers refer to like elements throughout the description of the figures.

Unless otherwise indicated, all numbers expressing quantities and conditions, and so forth used in the specification and claims are to be understood as being modified in all instances by the term "about." The terminology used herein is for the purpose of describing particular embodiments only and is not intended to be limiting of the present disclosure. As used herein, the singular forms "a," "an," and "the" are intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

The present disclosure is described below with reference to block diagrams and/or flowchart illustrations of methods, apparatus (systems and/or devices) and/or computer program products according to embodiments of the present disclosure. It is understood that a block of the block diagrams and/or flowchart illustrations, and combinations of blocks in the block diagrams and/or flowchart illustrations, may be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

Prior to describing the present disclosure in further detail, it will first be helpful to define various terms that will be used throughout the following discussion. For example:

The term "pacifier" may refer to at least any type of plastic or rubber device, having a nipple or shaped like a nipple, for an infant/baby/child to suck on.

The term "module" may refer to at least a self-contained component (unit or item) that is used in combination with other components and/or a separate and distinct unit of hardware or software that may be used as a component in a system, such as an analyzing system, including a pacifier assembly. The term "module" may also refer to at least a self-contained assembly of electronic components and circuitry, such as a stage in a computer that is installed as a unit. The term "module" may be used interchangeably with the term "unit."

The term "analyze" may refer to at least determining the elements or essential features or functions or processes of a plurality of analyzing modules in a pacifier assembly and/or to subject the plurality of analyzing modules in a pacifier assembly to computational processing. The term "analyze" may further refer to at least tracking data and/or collecting data and/or manipulating data and/or examining data and/or updating data and/or inspecting data and/or distinguishing data on a real-time basis in an automatic manner and/or a selective manner and/or manual manner (continuously, repeatedly, and/or intermittedly).

The term "storage unit" may refer to data storage. "Data storage" may refer to at least any article or material (e.g., a hard disk) from which information is capable of being reproduced, with or without the aid of any other article or device. "Data storage" may also refer to at least the holding of data in an electromagnetic form for access by a computer processor. Primary storage is data in random access memory (RAM) and other "built-in" devices. Secondary storage is data on hard disk, tapes, and other external devices. "Data storage" may also refer to at least the permanent holding place for digital data, until purposely erased. "Storage" implies a repository that retains its content without power. "Storage" mostly means magnetic disks, magnetic tapes and optical discs (CD, DVD, etc.). "Storage" may also refer to non-volatile memory chips such as flash, Read-Only memory (ROM) and/or Electrically Erasable Programmable Read-Only Memory (EEPROM).

The term "computing subsystem" may refer to at least any type of programmable machine, such as a computer, where the programmable machine may execute a programmed list of instructions and respond to new instructions that it is given. The term "computing subsystem" may also refer to a machine for performing calculations automatically or to a machine that manipulates data according to a list of instructions or to a programmable device that performs mathematical calculations and logical operations, especially one that may process, store and retrieve large amounts of data very quickly. The term "computing subsystem" may also refer to any type of device that stores and processes information, where the information is stored internally or externally either temporarily or permanently. The term "computing subsystem" may be used interchangeably with the term "processor."

The word "exemplary" is used herein to mean "serving as an example, instance, or illustration." Any embodiment described herein as "exemplary" is not necessarily to be construed as preferred or advantageous over other embodiments.

To this point, in conventional systems, breath analysis has been used solely for the detection of diseases and to methods of detecting, collecting, and inspecting breath samples for specific trace compounds. However, breath analysis has not been used for detecting molecules and/or volatile organic compounds in order to evaluate or derive or extract or acquire nutritional information from a device, such as a pacifier.

Researchers have shown that the chemical composition of expired breath may be an accurate, timely, and painless indicator of the health of an individual. For example, researchers have used light absorption and emission by molecules as a means for qualitatively identifying which molecules are present in a mixture, and quantitatively determining what concentration of each is present. Commonly, molecules with two or more atoms show distinct absorptions in the infrared region of the spectrum. The detailed characteristics of these absorptions may be extremely sharp at low pressure for molecules that are in the gas phase, enabling the accurate determination of organic compounds/molecules present in breath. However, as previously mentioned, breath analysis has been very limited to only diagnosing diseases by detecting molecules in alveolar breath only (further described below). Consequently, there is no system or method for using breath analysis to provide or extract or derive or acquire nutritional information from the breath (and saliva) and present it to a user, preferably in a continuous manner and in real-time.

The present disclosure refers to a system and method that enables the extraction of data/information from breath (or saliva) in order to determine or extract or derive nutritional information. The present disclosure further relates to a method of manufacturing a pacifier having breath and saliva data extraction capabilities for determining nutritional information. The present disclosure further relates to providing a means for detecting and quantifying one or more compounds of interest in the exhaled breath from a collected sample, storing such unique breath samples, analyzing input breaths for extracting or deriving nutritional information, and outputting the results to a user.

The present disclosure further discloses a chemical analysis method related to human breath. The present disclosure further teaches a method of collecting human breath samples, analyzing such human breath samples, storing such human breath samples, and utilizing such human breath samples to extract or derive nutritional information. The breath profile/breath concentration profile may contain a number of different molecules and/or organic compounds detected in human breath (either dead air space breath or alveolar breath or a combination thereof). For instance, human (and animal) breath contains hundreds of different trace volatile organic compounds (VOCs), in addition to the usual large amounts of $H_2O$ and $CO_2$. Thus, these types of VOCs would be valuable in creating a unique breath profile for a user and using that unique profile to determine or extract or derive or acquire nutritional information from the breath (or saliva) sampled collected.

Moreover, as mentioned above, there are two types of breath, that is, dead air space breath and alveolar breath. Dead air space breath is exhaled breath, whereas alveolar breath is breath located in the lungs. Dead air space breath may include hundreds, if not thousands, of different molecules/organic compounds. Also, alveolar breath may include hundreds, if not thousands, of different molecules/organic compounds.

However, few molecules/organic compounds in each type of breath are common to all individuals. In fact, the majority of molecules/organic compounds in each type of breath is unique and is contained in varying numbers and concentrations per individual. As a result, breath may provide a unique snapshot/fingerprint/blueprint/signature of an individual, thus identifying/distinguishing such individual, as does DNA (Deoxyribonucleic acid), for example. In particular, the main role of DNA molecules is the long-term storage of information. Similarly to DNA, breath stores/includes/encompasses information regarding an individual that is unique to that individual. By selectively counting unique molecules and/or organic compounds, and identifying such molecules and/or organic compounds, and measuring the concentration of each molecule and/or organic compound, a unique breath profile may be created that uniquely identifies or classifies or distinguishes or establishes or singles out a person and/or is used to provide or extract or derive nutritional information continuously and in real-time (or even intermittently in certain instances).

As a result, in the exemplary embodiments of the present disclosure, breath is used as a blueprint or fingerprint or signature to identify/distinguish the unique breath of, for example, the infant/child. The rich assortment of chemical substances present in an individual's breath may reveal a great deal about the person doing the breathing, including providing a unique snapshot or blueprint or signature of the organic compounds/molecules (number and concentration) exuded from one's breath to determine or extract or derive nutritional information.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments will be described below while referencing the accompanying figures. The accompanying figures are merely examples and are not intended to limit the scope of the present disclosure.

Figure 1A:
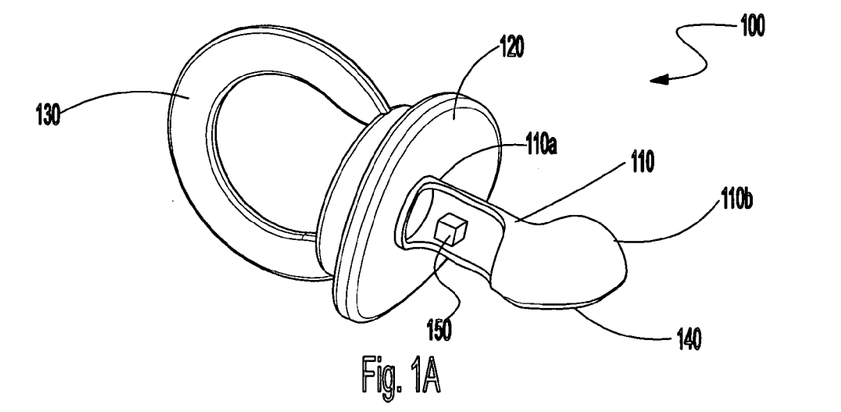
FIG. 1A is a perspective view of a pacifier assembly including a breath analysis module, in accordance with the present disclosure.
Figure 1B:
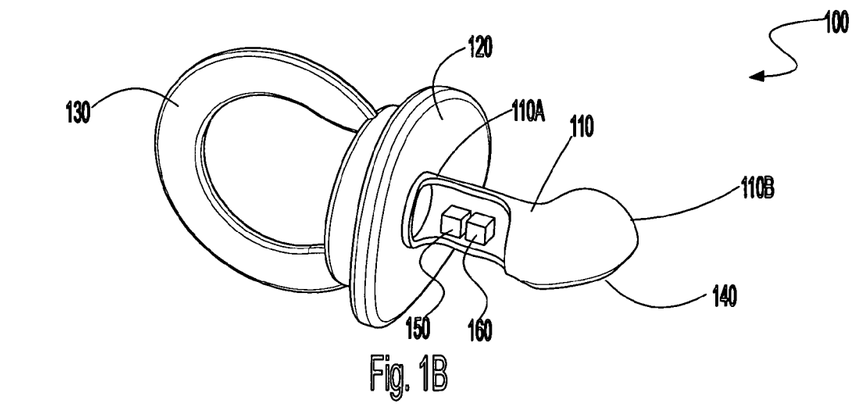
FIG. 1B is a perspective view of a pacifier assembly including a breath analysis module and a saliva analysis module, in accordance with the present disclosure.
Figure 1C:
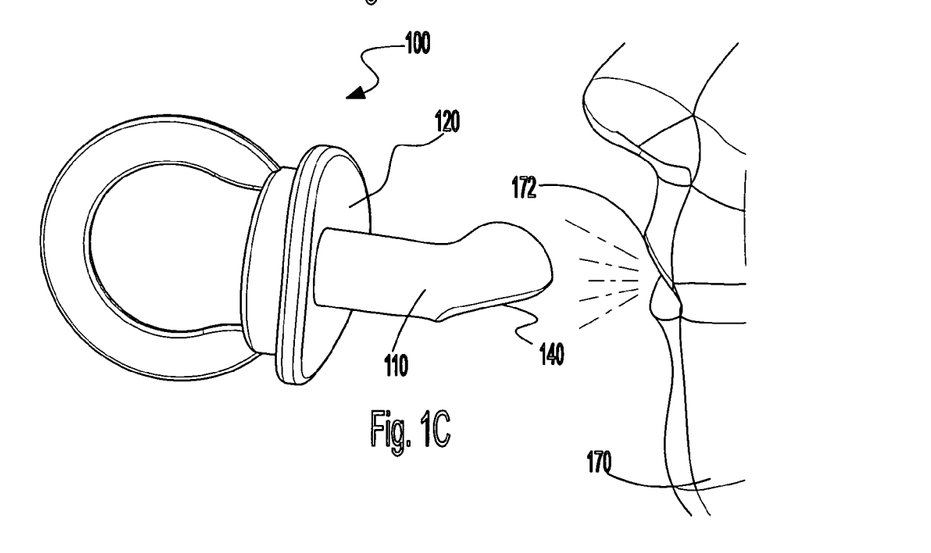
FIG. 1C is a perspective view of the pacifier assembly of FIG. 2 being inserted into an infant's/child's mouth for collecting, analyzing, and storing breath and saliva samples, in accordance with the present disclosure.

With reference to FIGS. 1A-1C, there is presented a perspective view of a pacifier assembly including a breath analysis module and/or saliva analysis module to be inserted into, for example, an infant's/child's mouth, in accordance with the present disclosure.

The pacifier assembly 100 of FIG. 1A includes a nipple 110 connected to a base portion 120. The base portion 120 may be optionally connected to a grip portion 130. The nipple includes a lower portion 110a and an upper portion 110b. The upper portion 110b includes a breath analysis module 150 configured to receive breath samples from a user (e.g., an infant or child) via an orifice 140. The orifice or opening or slit 140 may be centrally positioned on the nipple 110. Additionally, FIG. 1B illustrates a saliva analysis module 160, which may be utilized in conjunction with the breath analysis module 150.

In operation, as shown in FIG. 1C, the detecting and collecting of organic compounds/molecules in a breath sample may include a person 170 (e.g., an infant or child) breathing or exhaling into the orifice 140 of the nipple 110 of the pacifier 100 to absorb at least one breath molecule/volatile organic compound. The breath 172 is collected in an exhaled breath collector located in the breath analysis module 150. The breath analyzing module 150 analyzes the breath sample and extracts one or more molecules and/or organic compounds. This data may be stored in a storage unit, as discussed below with reference to FIG. 6, such as a memory, as defined herein. The results of the breath analysis module 150 may be used to trigger the display of nutritional information (see FIGS. 5A and 5B) based on the number and concentration of molecule/volatile organic compound found/discovered in the breath samples collected.

Nutrition (also referred to as nourishment or aliment) is the provision, to cells and organisms, of the materials necessary (in the form of food) to support life. Nutritional science investigates the metabolic and physiological responses of the body to diet.

The human body contains chemical compounds, such as water, carbohydrates (sugar, starch, and fiber), amino acids (in proteins), fatty acids (in lipids), and nucleic acids (DNA and RNA). These compounds in turn consist of elements such as carbon, hydrogen, oxygen, nitrogen, phosphorus, calcium, iron, zinc, magnesium, manganese, and so on. All of these chemical compounds and elements occur in various forms and combinations in the human body. The human body consists of elements and compounds ingested, digested, absorbed, and circulated through the bloodstream to feed the cells of the body.

In general, there are six major classes of nutrients: carbohydrates, fats, minerals, protein, vitamins, and water. In the exemplary embodiments of the present disclosure, nutritional information may refer to these nutrients, and at least to one of carbohydrates, fats, minerals, protein, fiber, vitamins, water, salt, sugar, sodium, antioxidants, and phytochemicals.

Additionally, a respiratory quotient may be computed. The respiratory quotient (or RQ or respiratory coefficient), is a unit-less number used in calculations of basal metabolic rate (BMR) when estimated from carbon dioxide production. Such measurements, like measurements of oxygen uptake, are forms of indirect calorimetry. RQ value corresponds to a caloric value for each liter (L) of $CO_2$ produced. If $O_2$ consumption numbers are available, they are usually used directly, since they are more direct and reliable estimates of energy production. As such, one or more sensors (see FIG. 4) may be positioned about the pacifier assemblies 100 to measure at least one of pressure, humidity, temperature, oxygen levels, oxygen inhaled, oxygen exhaled, and carbon dioxide consumed. Thus, the one or more sensors may be configured to compute at least one of: (i) a difference between the oxygen inhaled and the oxygen exhaled, (ii) the oxygen levels of each of the breath samples received from the user via the nipple, and (iii) a respiratory quotient.

Therefore, in operation, as shown in FIG. 1C, the breath 172 of an infant/child 170 is sampled and collected. The breath 172 may be analyzed for a specified or pre-defined or predetermined number of VOCs by the breath analysis module 150. The VOCs are analyzed to determine or extract or derive nutritional information. The analysis module 150 may include a database of VOCs that indicate specific conditions of the infant/child 170. These conditions may include, but are not limited to, hunger, thirst, dehydration, and lack of nutrients (e.g., carbohydrates, fats, minerals, protein, fiber, vitamins, water, salt, sugar, sodium, antioxidants, and phytochemicals). As a result, the parent is able to properly determine whether the infant/child 170 has received the appropriate nutrients necessary for growth on a continuous basis (e.g., hourly, daily, weekly, monthly, yearly, etc.).

For example, it is preferable that common molecules and/or organic compounds be selected for comparison. There may be hundreds or even thousands of molecules and/or organic compounds from which to select a number of desirable combinations for comparison purposes. For example, 100 common organic compounds may be selected to form a unique breath profile for a person. However, 200, 300 or even 400 common organic compounds may be selected to form a unique breath profile for a person. In addition, 200 unique molecules and 200 unique organic compounds may be selected to form a unique breath profile for a person.

In other words, any uncommon/common organic compounds may be selected, any uncommon/common molecules may be selected, or any combination of molecules and organic compounds may be selected to form any type of desirable unique breath profile (number of items and concentration of items may be examined). Of course, any type of variables may be measured and/or identified and/or collected that would be satisfactory for creating any type of unique breath profile pertaining to a person. One skilled in the art could envision using any chemical analysis techniques and using any chemical variables with any type of chemical characteristics to obtain a preferred unique breath profile for extracting or deriving nutritional information.

For example, regarding dehydration, the symptoms of mild dehydration include not just thirst, but also dizziness, headaches, muscle aches and pains, lethargy, fatigue, an uncomfortably dry or sticky feeling in the mouth, less frequent urination, and a reduced urine output. Baby dehydration becomes evident when the baby's urine output decreases sharply (as indicated by fewer diapers). Severe dehydration, which is considered a medical emergency in both children and adults, may cause enormous thirst, mental confusion, extremely dry skin and mouth, very little perspiration, reduced blood pressure, very low urine output, very dark yellow urine, heart palpitations, fevers. However, by the time the majority of these symptoms are detected it is too late. Additionally, parents may also only guess whether their babies/young children have aches or pair or experience fatigue and dizziness because an infant/child is not capable of conveying such information to the parent. As such, the exemplary embodiments of the present disclosure get rid of the guessing game and enable the parents to timely and accurately detect a condition or state or status of an infant/child based on the nutritional information derived or extracted from the pacifier assembly 100 (see FIGS. 1A-1C). Moreover, the parents may have better control of the baby's/child's weight management by providing the infant/child with the appropriate amounts of nutrients, based on the breath profile derived.

In summary, the pacifier assembly 100 may be used to indicate to the parents whether the child is, for example, hungry or thirsty or dehydrated or overfed or underfed. An infant or child may be feeling hungry or thirsty or dehydrated and is not able to convey such information to the parent. As such, the parent simply guesses to the nature of the infant's/child's needs. As a result, the infant/child may be overfed or may not be fed enough or may not be amply hydrated. Therefore, the infant/child may not receive the appropriate level of nutrients (nourishment) he/she requires. However, the pacifier assembly 100 of the exemplary embodiments may be used to indicate the parents whether the infant/child is, for example, hungry or thirsty or dehydrated based on the nutritional information collected from the breath samples (and/or saliva samples) provided by the infant/child. The notification or indication means will be described below in detail with reference to FIGS. 5A and 5B.

Moreover, the exemplary embodiments of the present disclosure provide for instant breath analysis or on-the-spot breath analysis or immediate, instantaneous, and prompt breath analysis. Chemical breath analysis may be performed directly within the nipple of a pacifier, thus creating a portable chemical breath analysis system or configuration. Thus, a direct relationship is established between the chemical composition of breath and nutritional information/data to create a unique breath profile or a plurality of breath profiles for a single user or a plurality of users, capable of being compared to each other to determine historical deviations of nourishment received (discussed below).

Figure 2A:
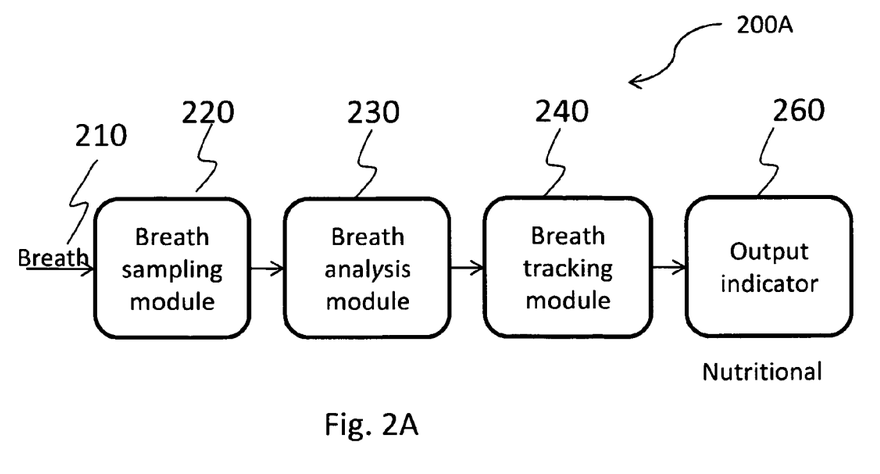
FIG. 2A is a block diagram illustrating a flow sequence of analyzing breath via the pacifier assembly of FIG. 1A, in accordance with the present disclosure.
Figure 2B:
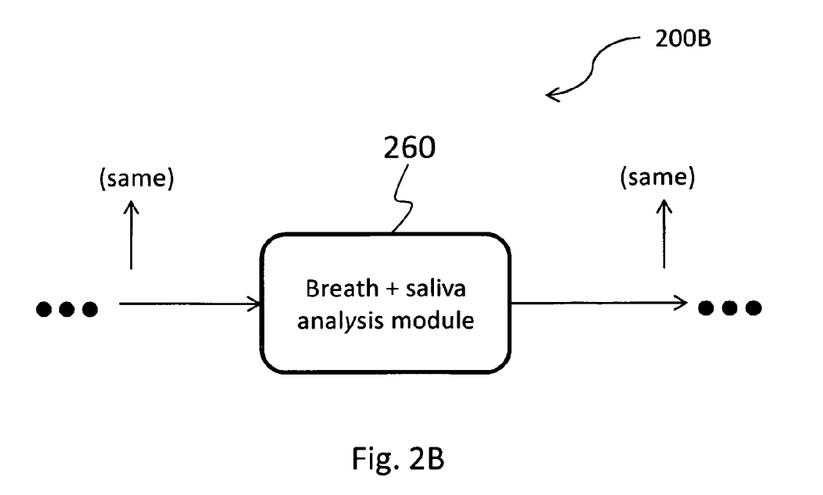
FIG. 2B is a block diagram illustrating a flow sequence of analyzing breath and saliva in conjunction via the pacifier assembly of FIG. 1B, in accordance with the present disclosure.

With reference to FIG. 2A, there is presented a block diagram illustrating a flow sequence of analyzing breath via the pacifier assembly, in accordance with the present disclosure. With reference to FIG. 2B, there is presented a block diagram illustrating a flow sequence of analyzing breath and saliva in conjunction via the pacifier assembly, in accordance with the present disclosure.

The block diagram 200A depicts breath 210 as an input. The breath 210 is sampled via the breath sampling module 220 and then analyzed via the breath analysis module 230. The breath 210 may be recorded and/or tracked via the recording/tracking module 240. A nutrition output indicator 250 outputs and/or displays nutritional information based on the sampled and analyzed breath 210 (see FIGS. 5A and 5B).

The breath sampling module 220 receives one or more breaths 210 and takes one or more samples from those breaths 210. The samples may be a section, a fragment, an instance, a part, a pattern, a piece, a portion, a segment or a unit of breath 210. Several samples may be extracted for accuracy and a portion of each sample may be used or a portion of select samples may be used. In other words, the breath sampling module 220 may receive several input breaths 210 and selectively decide which breaths 210 to accept. The breath sampling module 220 may accept one sample from one breath or a plurality of samples from several breath inputs from the same user. One skilled in the art may contemplate using a plurality of different scenarios or configurations in order to manipulate the most appropriate breath samples.

The breath analyzing module 230 analyzes the one or more samples of breath provided by the breath sampling module 220. The breath analysis may be executed by using any type of breath analysis techniques, such as spectroscopy/spectrometry and/or gas chromatography. One skilled in the art may envision any type of suitable breath analysis techniques.

For example, spectroscopy pertains to the dispersion of an object's light into its component colors (i.e., energies). By performing this dissection and analysis of an object's light, researchers may infer the physical properties of that object (such as temperature, mass, luminosity, number of molecules, number of organic compounds, and composition or concentration of molecules/organic compounds). Spectrometry is the spectroscopic technique used to assess the concentration or amount of a given species. In those cases, the instrument that performs such measurements is a spectrometer or spectrograph. Spectroscopy and/or spectrometry are often used in physical and analytical chemistry for the identification of substances through the spectrum emitted from or absorbed by them. Mass spectroscopy is a detection method, which may be coupled with chromatography or sample directly from the headspace of a sample, which ionizes, fragments, and rearranges a molecule under a given set of conditions and makes identification of the molecular weight/charge (m/z) of molecules possible.

However, any type of spectrometry and/or spectroscopy may be used, such as, but not limited to, electromagnetic spectroscopy, electron spectroscopy, mass spectroscopy, absorption spectroscopy, emission spectroscopy, infrared spectroscopy, ultraviolet spectroscopy, thermal spectroscopy, laser spectroscopy, and/or scattering spectroscopy. One skilled in the art may envision any type of spectroscopy and/or spectrometry techniques used to analyze breath from breath samples.

Chromatography pertains to a broad range of physical methods used to separate and or to analyze complex mixtures. The components to be separated are distributed between two phases: a stationary phase bed and a mobile phase which percolates through the stationary bed. Chromatography is a collective term for a family of laboratory techniques for the separation of mixtures. It involves passing a mixture dissolved in a "mobile phase" through a stationary phase, which separates the analyte to be measured from other molecules in the mixture and allows it to be isolated. Chromatography is the physical separation of two or more compounds based on their differential distribution between two phases, the mobile phase and stationary phase. The mobile phase is a carrier gas that moves a vaporized sample through a column coated with a stationary phase where separation takes place. When a separated sample component elutes from the column, a detector, such as a Flame Ionization Detector (FID) or an Electrochemical Detector (ECD), converts the column eluent to an electrical signal that is measured and recorded.

However, any type of chromatography may be used, including, but not limited to, gas chromatography, affinity chromatography, and/or ion exchange chromatography. One skilled in the art may envision any type of chromatography techniques used to analyze breath from breath samples.

Therefore, the present disclosure is not limited to only these two types of breath analysis techniques. Any type of breath analysis technique or combination thereof may be used to analyze breath samples from humans, animals, and/or plants.

In the exemplary embodiments of the present disclosure, breath analysis may refer to extracting a number of molecules and/or a number of organic compounds and/or a concentration for each of the molecules and/or organic compounds. The breath analyzing module 230 may be pre-programmed to selectively choose which of the plurality of molecules and/or organic compounds to use for creating a unique breath profile. The breath analyzing module 230 may choose select uncommon molecules and/or uncommon organic compounds to create a unique breath profile. The breath analyzing module 230 may identify the concentration of each select uncommon molecule and/or organic compound. The unique breath profile may be created by using a plurality of different variables contained in breath that would be deemed satisfactory to provide for a unique breath profile. The exemplary embodiments are not limited to any specific variables or to any specific concentration of variables. All these variables may be predetermined/preset (factory settings/default settings) or may be uniquely prepared/modified based on the user.

Additionally, the breath analyzing module 230 may use/manipulate any type of electronic means/electronic devices to analyze the breath sample provided by the breath sampling module 220. For example, any type of microprocessor or processor or computing subsystem, as defined herein, may be used to execute such operations.

Optionally, in an alternative embodiment, the analyzing module 230 may further determine whether there is a match between a unique breath sample saved in the memory device (e.g., storage unit) and a second breath received via the orifice 140 of the nipple 110. In other words, several breaths from several different infants/children may be entered via the same orifice 140 and a determination may be made whether any of those subsequent breath samples matches the first breath sample in order to determine who the infant is and thus provide the appropriate nutritional information for the correct infant.

The analyzing module 230 may then communicate with the nutritional output indicator module 250 to provide for a means of informing the user regarding the extraction of nutritional information, such as, for example, carbohydrates, fats, minerals, protein, fiber, vitamins, water, salt, sugar, sodium, antioxidants, and phytochemicals. Such nutritional information may be used to determine whether the infant/child is, for example, hungry or thirsty or dehydrated or overfed or underfed or predict any other condition or state or status (not a disease) of the child (i.e., nutritional well-being, nutritional health, nutritional energy, nutritional strength, nutritional soundness, etc.).

The recording/tracking module 240 may record and track the breath input activity. In other words, each time a breath sample is entered via the orifice 140 of the nipple 110 of the pacifier assembly 100 (see FIGS. 1A-1C), an instance of such input may be recorded and saved in the memory device or storage unit, as defined herein. Such information may be transmitted (wired or wirelessly) to a computing subsystem (such as a personal computer (PC) or other mobile devices, such as a cell phone), where the authorized user may track the historical data related to nutritional information related to an infant/child. Additionally, the original breath profile of the authorized user may be monitored for slight deviations and the electronic processing means may decide to provide slight/minor updates to the existing original breath profile based on any deviations experienced. This may be executed in an automatic manner by the electronic processing means located in the breath analysis module 230. Therefore, nutritional information may be transmitted to any type of portable or non-portable electronic device in order to allow, for example, parents to monitor the health of their babies/children via the use of the pacifier assemblies.

The output indicator module 250 may be a visual or an audible or a combination of a visual and audible indication means. The visual indicator may be a light emitting diode (LED) operating in a plurality of modes and/or colors and/or patterns. The indicator display may be located on the back surface or base portion 130 of the pacifier assembly 100 (see FIGS. 1A-1C and FIGS. 5A-5B). However, it is envisioned that one skilled in the art may position the indicator display on any portion of the pacifier assembly 100 in accordance with design preferences. The indicator display may display any type of information or indicia or patterns in any simple or complicated manner, based on design preferences.

Referring to FIG. 2B, a breath and saliva analyzing module 260 is presented. Therefore, in addition to analyzing breath, the pacifier is capable of analyzing saliva samples in combination or in conjunction with breath. The term "saliva" may refer to any type of spit, spittle, drivel, drool, etc. Saliva may refer to the watery and usually frothy substance produced in the mouths of humans and most other animals. Saliva may be a component of oral fluid. Human saliva is composed of 98% water, while the other 2% consists of other compounds such as electrolytes, mucus, antibacterial compounds, and various enzymes. Saliva is a fluid that may contain at least water, electrolytes (e.g., sodium, potassium, calcium, magnesium, chloride, phosphate, iodine, etc.), mucus, anti-bacterial compounds, enzymes, proline-rich proteins, bacterial cells, bacterial products, and opiorphin. It is contemplated to use such informational content from saliva in combination with breath samples (i.e., VOCs) in order to help extract or derive nutritional information related to, for example, an infant/child using a pacifier assembly 100 (see FIGS. 1A-1C).

Figure 3:
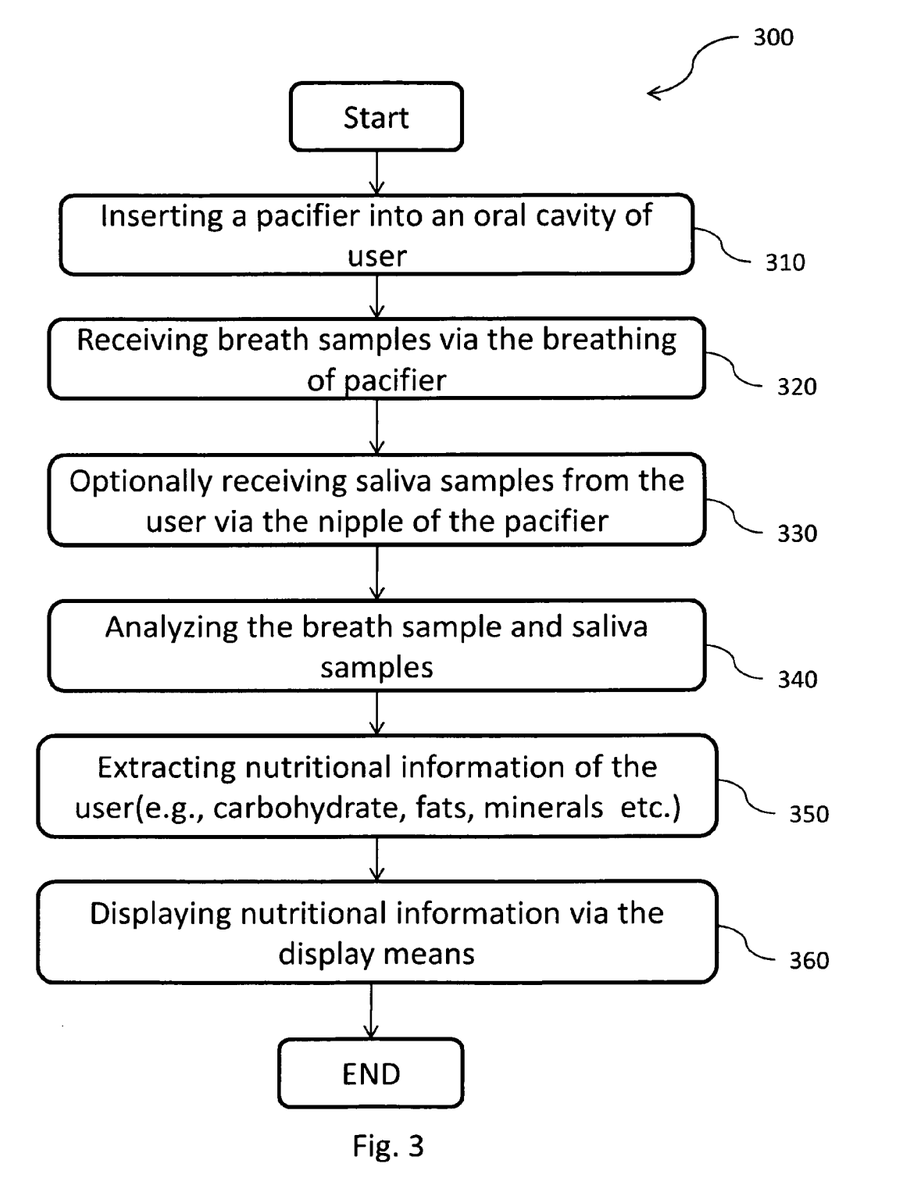
FIG. 3 is a flowchart illustrating receiving, collecting, and analyzing breath and saliva samples from an infant/child via the pacifier assembly of FIGS. 1A-1C, in accordance with the present disclosure.

With reference to FIG. 3, there is presented a perspective view of a flowchart illustrating receiving breath and saliva samples from, for example, an infant/child via the pacifier assembly, in accordance with the present disclosure.

The flowchart 300 includes the following steps. In step 310, a pacifier is inserted into an oral cavity of a user (e.g., infant/child). In step 320, breath samples are received from the user via the nipple of the pacifier assembly. In step 330, saliva samples may be optionally received from the user via the nipple of the pacifier assembly. In step 340, the breath samples and the saliva samples are analyzed via a breath and saliva analysis module. In step 350, nutritional information of the user is extracted, such as carbohydrates, fats, minerals, protein, fiber, vitamins, water, salt, sugar, sodium, antioxidants, and phytochemicals. In step 360, nutritional information is displayed via a display means (e.g., one or more strips). The process then ends. It is to be understood that the method steps described herein need not necessarily be performed in the order as described. Further, words such as "thereafter," "then," "next," etc. are not intended to limit the order of the steps. These words are simply used to guide the reader through the description of the method steps.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

Accordingly, blocks of the flowcharts support combinations of structures for performing the specified functions and combinations of steps for performing the specified functions. It will also be understood that each block of the flowcharts, and combinations of blocks in the flow charts, may be implemented by special purpose hardware-based computer systems, which perform the specified functions or steps, or combinations of special purpose hardware and computer instructions.

Figures 4, 5A, 5B:
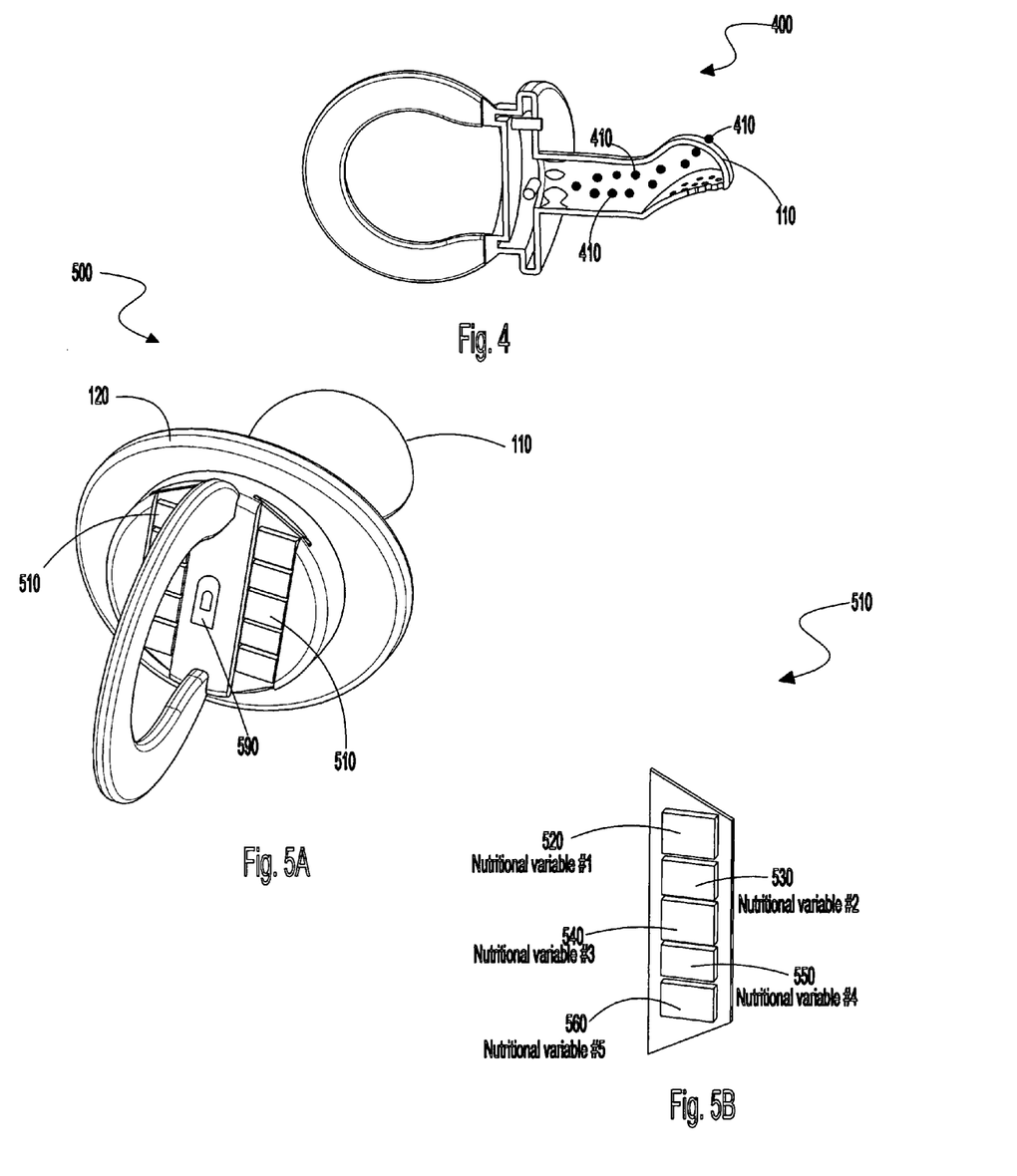
FIG. 4 is a perspective view of the pacifier assembly of FIG. 1 including a plurality of sensors positioned thereon and/or embedded therein, in accordance with the present disclosure.
FIG. 5A is a rear, perspective view of the pacifier assemblies of FIGS. 1A-1C including at least one strip indicating nutritional information derived from the breath and/or saliva samples of the infant/child, and including at least electromechanical connecting mechanism, in accordance with the present disclosure.
FIG. 5B is a front view of the at least one strip indicating nutritional information derived from the breath and/or saliva samples of the infant/child, in accordance with the present disclosure.

With reference to FIG. 4, there is presented a perspective view of the pacifier assembly of FIGS. 1A-1C including a plurality of sensors positioned thereon and/or embedded therein, in accordance with the present disclosure.

The pacifier assembly 400 illustrates a plurality of sensors 410 positioned on the nipple 110 and/or embedded within the nipple 110. The sensors 410 may be any type of oxygen sensors or chemical sensors. In addition, several vapor sensing technologies, including conducting polymers, electrochemical cells, infrared spectroscopy, ion mobility spectrometry, metal oxide semiconductor, photo-ionized detectors, Fourier transforms, non-dispersive infrared spectrometry, elected ion flow tubes, and surface acoustic wave sensors, have been evaluated for detection of compounds in breath. Sensor sensitivity, selectivity, operating life, shelf-life, drift, linearity, initial cost, recurring costs, warm-up time, analysis time, power consumption, portability and calibration needs may also be evaluated to decide on the desired technique.

With reference to FIG. 5A, there is presented a rear, perspective view of the pacifier assemblies of FIGS. 1A-1C including at least one strip indicating nutritional information derived from the breath and/or saliva samples of, for example, the infant/child, in accordance with the present disclosure. FIG. 5B is a close-up view of the strips shown in FIG. 5A.

Referring to FIG. 5A, the indicator strips 510 may be a visual indicator, an audible indicator, and/or a combination of a visual and audible indicator. The visual indicator may be a light emitting diode (LED) operating in a plurality of modes and colors. The indicator strips 510 may be located on the back surface of the base portion 120 of the pacifier assembly 500. However, it is envisioned that one skilled in the art may position the indicator strips 510 on any portion of the pacifier assembly 500 in accordance with design preferences.

The indicator strips 510 may display any type of information in any simple or complicated manner. For example, the words, "variable one adequate" and "variable two inadequate" may be displayed to indicate the result or the words "good" and "bad" may be displayed to indicate the nutritional information results. However, any type of message or text or pattern conveying any type of information may be indicated on the indicator strips 510. Also, the indicator strips 510 may be of any size imaginable, from a few millimeters to a few inches and constructed from any type of materials (LEDs, LCDs, or flexible displays). In addition, the indicator strips 510 may be optional.

With continued reference to FIG. 5B, an exemplary strip 510 is illustrated. The strip 510 may be a series of abutting (or adjacent) areas (or spaces or domains or regions or zones) each configured to include a separate and distinct indication of a nutritional variable or value. For example, the first area 520 may indicate a first nutritional value (e.g., water), the second area 530 may indicate a second nutritional value (e.g., protein), the third area 540 may indicate a third nutritional value (e.g., salt), the fourth area 550 may indicate a fourth nutritional value (e.g., sugar), and the fifth area 560 may indicate a fifth nutritional value (e.g., fiber). Of course, one skilled in the art may contemplate using a plurality of different areas to display a variety of different nutritional variables and/or values.

It is also noted that the indicator strips 510 may be removable and replaceable. In other words, the indicator strips 510 may be sold separately and inserted by the user into one or more pacifier assemblies 500. The indicator strips 510 may be attached to or incorporated with the one or more pacifier assemblies 500 in any manner conceivable by one skilled in the art. Moreover, the indicator strips 510 may have a quick response time (seconds or minutes) and are easy to read and detect the colors or patterns or text or messages displayed thereon. Additionally, it is contemplated that more than one indicator strip 510 may be positioned on each pacifier assembly 500. Also, it is contemplated that the indicator strips 510 are equally spaced apart from each other and each may indicate a number of nutritional information. For example, 4 strips may be presented, each indicating 2 nutritional variables. One skilled in the art may contemplate a plurality of different strips and strip configurations to provide nutrition information output to a user.

Moreover, the base portion 120 may include a connector 590. The connector 590 may be a Universal Serial Bus (USB) port. The connector 590 may be a mini-USB port for receiving a USB flash drive (not shown). The USB flash drive consists of a flash memory data storage device integrated with a USB interface. USB flash drives are typically removable and rewritable. Of course, any type of portable memory or storage means may be connected to the pacifier assemblies of the exemplary embodiments. Additionally, it is contemplated that the pacifier assemblies of the exemplary embodiments may be connected directly to a computing means or any other electronic device.

The term "electronic device" may refer at least to one or more personal computers (PCs), a standalone printer, a standalone scanner, a mobile phone, an MP3 player, audio electronics, video electronics, GPS systems, televisions, recording and/or reproducing media (such as CDs, DVDs, camcorders, cameras, etc.) or any other type of consumer or non-consumer analog and/or digital electronics. Such consumer and/or non-consumer electronics may apply at least in any type of entertainment, communications, home, and/or office capacity. Thus, the term "electronic device" may refer to any type of electronics suitable for use with a circuit board and intended to be used by a plurality of individuals for a variety of purposes. The electronic device may be any type of computing and/or processing device.

Additionally, "electronic devices" may refer to at least, or may include but are not limited to, a mouse, keyboard, Bluetooth™ adapter, global positioning system (GPS) receiver, remote control, audio module, user interface module, electronic-book reader module, radio frequency identification (RFID) reader, barcode reader, digital projector, universal serial bus stick, magnetometer, fingerprint reader, current/voltage measuring device, electrocardiogram, pulse measuring device, and stethoscope. Additionally, "electronic devices" may refer to at least, or may include but are not limited to, an electronic book, displays, television sets, electronic paper, watches, electronic calculators, cellular phones, personal digital assistants, cellular telephone, view finder, direct view type video tape recorder, car navigation system, pager, electronic notebook or personal computer (PC), electric calculator, word processor, work station, picture telephone, point of sale (POS) terminal(s), point-of-entry (POE) terminal(s) and any type of electrical or mechanical or electromechanical apparatus/system/configuration with one or more touch panels.

Therefore, the exemplary pacifier assemblies of the present disclosure may include any type of connector mechanism to connect to any type of electronic device, as defined herein, in a wireless or non-wireless manner in order to bi-directionally exchange information with one or more electronic devices.

Figure 6:
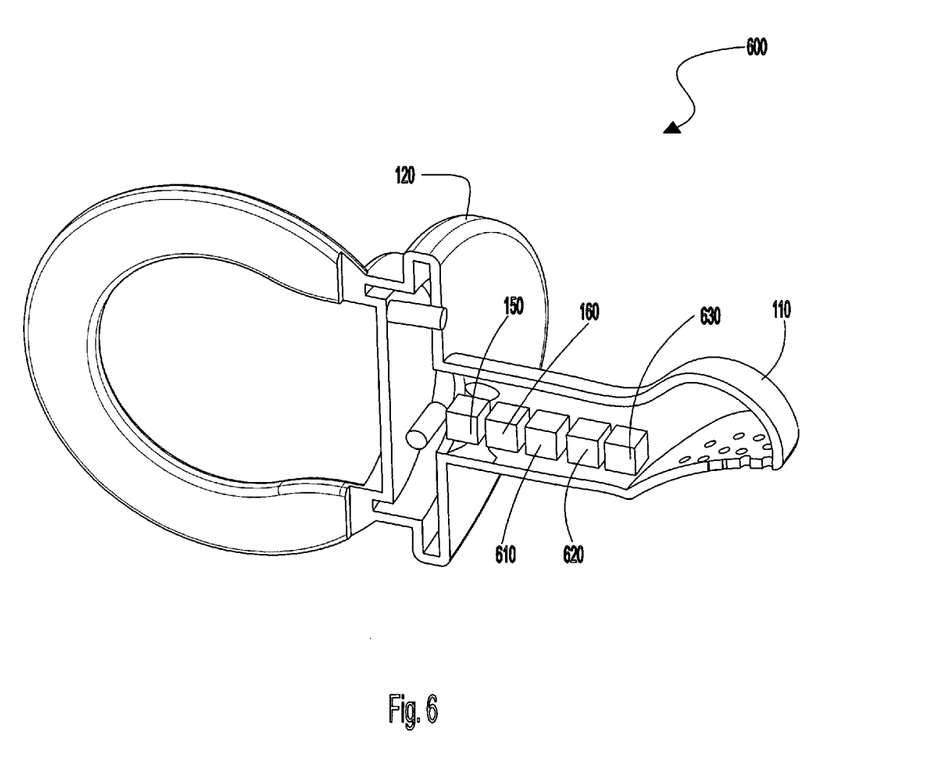
FIG. 6 is a perspective view of the pacifier assemblies of FIGS. 1A-1C including at least sound emitting capabilities, a storage unit, and/or a filtering mechanism (or air purifier), in accordance with the present disclosure.

With reference to FIG. 6, a perspective view of the pacifier assemblies of FIGS. 1A-1C including sound emitting capabilities, a storage unit, and/or a filtering mechanism (or air purifier), in accordance with the present disclosure is presented.

Pacifier assembly 600 includes a sound emitting mechanism 610, a filter mechanism 620 (or air purifying means), and a storage unit 630. One or more of such units may be incorporated with or into any of the exemplary embodiments of the present disclosure. Additionally, one or more processors may be incorporated with any of the pacifier assemblies of the present disclosure.

The sound emitting mechanism 610 may be configured to emit sounds based on the breath samples received from the user via the nipple of the pacifier assembly 600. For example, if one of the nutritional variables or values does not fall within the proper range, a first sound may be emitted to indicate to the parent that a nutritional issue has arisen. For example, the sound emitting mechanism 610 may emit a second sound if further samples are required in order to acquire a more accurate reading. One skilled in the art may contemplate a sound emitting mechanism 610 activated by any number of factors based on breath (or saliva) samples inputted.

The filtering mechanism 620 may be an air purifying mechanism for eliminating respirable airborne contaminants (e.g., dust, smoke, allergens, mold, pet dander pollution, etc.) in the atmosphere. The sucking motion of the infant/child may activate the filtering mechanism 620. The filtering mechanism 620 may be incorporated within the nipple of the pacifier assembly 600. Moreover, the filtering mechanism 620 may be any type of air purifying mechanism. Air purifiers are designed to clean the air by filtering out harmful particles and air pollutants like allergens, mold, pet dander pollution and dust.

The storage unit 630 may be located within the pacifier assembly 600. However, it is contemplated than an external storage device may be utilized in conjunction with an internal storage device, where the two storage devices communicate via wireless means. In other words, an external storage device may be located in a doctor's office, where the user (or patient) inputs a breath sample and that breath sample may be transferred from the external device to the internal storage device located in the pacifier assembly 600.

Therefore, in summary, analysis of breath samples (or saliva samples) for diagnostic purposes or non-diagnostic purposes has the advantage that the breath sample to be analyzed is collected from the user in a non-invasive manner with a minimum of discomfort or inconvenience. In general, the trend in medicine is toward more non-invasive testing. Since breath is the only biological fluid that may be obtained non-invasively and on demand, it is currently the matrix of choice for a number of applications, well beyond pacifier assemblies. As a result, since the human body includes chemical compounds, and such chemical compounds include nutrients, the content of nutrients may be determined or extracted from or derived from the breath of the person to output accurate nutritional information values (or nutritional feedback), continuously and in real-time (or intermittently in certain instances).

Optionally, any type of timing requirements may be programmed and saved into the pacifier assemblies of the exemplary embodiments of the present disclosure. For example, the sound emitting mechanism may emit a sound to indicate that a reading should take place, for instance, every 2 hours, every 4 hours, every day in the morning and evening, etc. The timing requirements may be automated or may be programmed by the parents.

Optionally, the obtained breath profile may be compared to a generic breath profile stored in a database. A user's breath profile may be compared against a generic breath profile that indicates required nutrition information. Therefore, parents may be able to compare their baby's/child's breath profile to that of other babies/children. The parent may input the infant's/child's age and receive information regarding the nutritional information of the average child of that age. In an alternative embodiment, the breath profile may be compared against a breath profile previously stored in pacifier itself by a specific and unique user. The breath profiles may be unique to a user since they are derived from one user, not a group of users displaying the same characteristics (such as a particular disease). As such, the parents may compare the current nutritional information derived to previous or historical information. Nutritional information of several years may be stored in the storage unit.

Optionally, data from a particular user may be stored so that multiple samples over an extended period of time may be taken. This permits a baseline to be established for a particular user, and trend analysis may be performed on the resulting data, relative to the database of breath profiles. If there is an acute and significant change in the chronic condition of the user's breath, indications of this change may be communicated to a physician or healthcare provider or to the parent of the user. In other words, this is a dynamic system that allows for updated/revised breath profiles to be stored based on a user's changed nutritional circumstances.

Optionally, the nutritional information stored in one pacifier assembly may be wirelessly transferred to another pacifier assembly. Since a baby/child may have several pacifiers, the data may be readily transmitted between pacifier assemblies.

Optionally, there may be one orifice or nipple that accepts more than one unique profile. In other words, 2 or 3 breath profiles of 2 or 3 different individuals may be programmed into the memory or storage unit. All the users may use the same orifice or separate orifices may be provided for each user breath profile.

Optionally, the pacifier assemblies may include a reset button that allows the parents to reset the user's breath profile.

Optionally, the pacifier of the present disclosure may be constructed of a clear or transparent or translucent material in order to better identify the content contained within the pacifier assemblies.

Figure 7:
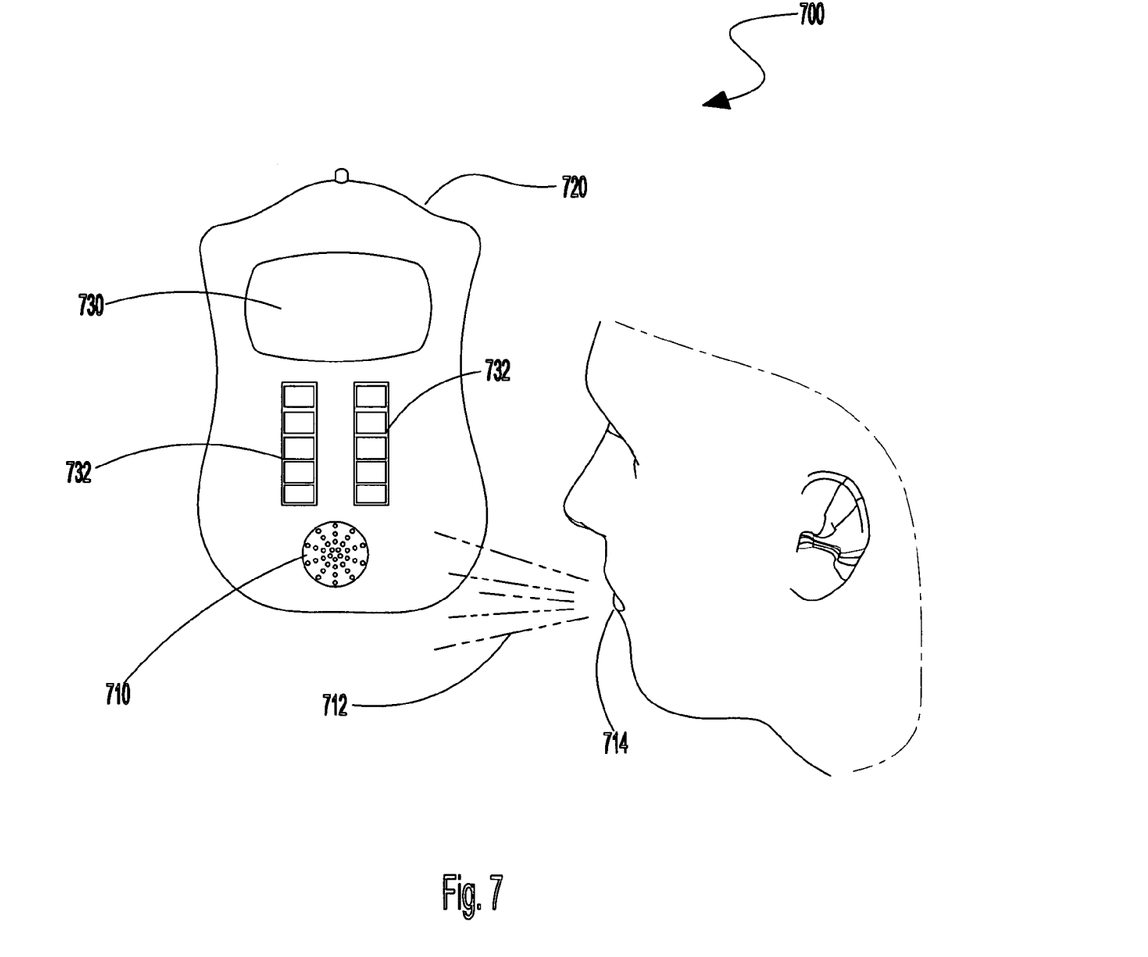
FIG. 7 is a perspective view of a portable nutritional information device including a breath analysis module (and/or a saliva module) for extracting or deriving nutritional information of a user, in accordance with the present disclosure.

Referring to FIG. 7, in an alternative embodiment, the concepts of the exemplary embodiments of the present disclosure may be expanded to adults. In other words, the pacifier may be replaced as a portable nutritional information device 700 including at least one orifice 710 for receiving breath samples 712 from a user 714 in order to provide nutritional information to the user 714. For example, the user 714 may be an athlete or an individual who exercises often and wishes to monitor his/her nutritional content intake. As such, nutritional information may be constantly provided or output by having the user 714 input breath samples 712 into the nutritional information device 700.

Therefore, the nutritional information device 700 may be presented including an orifice 710 configured to receive a plurality of breath samples 712 from a user 714, a base member 720 configured for attachment to the orifice 710 and an output mechanism 730 attached to the base member 720 and configured for displaying different nutritional information values based on the plurality of breath samples 712 received, the output mechanism 730 having one or more removable strips 732. The plurality of breath samples 712 received from the user 714 via the orifice 710 are analyzed for nutritional information, the nutritional information including at least one of carbohydrates, fats, minerals, protein, fiber, vitamins, water, salt, sugar, sodium, antioxidants, and phytochemicals.

The nutritional information device 700 may include a plurality of orifices for inputting several breath samples of several users. It is contemplated that saliva samples may also be collected by the nutritional information device 700. All the features discussed herein with regards to the pacifier (as discussed above with reference to FIGS. 1A-6) may be presented or associated with or incorporated with the nutritional information device 700 for adults. The nutritional information device 700 may be a separate and distinct device or may be removably attachable to an electronic device, such as a mobile device (e.g., cell phone, Smart Phone, iPhone®, Blackberry®, telecommunication device, etc.) or any other electronic device as defined herein. The nutritional information device 700 may be embedded with an electronic device, such as a mobile device. Additionally, the nutritional information device 700 may communicate (wired or wirelessly) with any type of electronic device, as defined herein, for transmitting nutritional information related to the users inputting breath samples.

Referring back to FIGS. 1A-6, all the pacifiers of the present disclosure are not limited to any particular shape or design. Although the pacifiers are described and depicted herein as being generally cylindrical or nipple-shaped, the configuration of the pacifiers is a matter of design choice. The use of generally cylindrical or nipple-shaped pacifiers is described because it gives the pacifiers a readily acceptable appearance and shape, and because generally cylindrical or nipple-shaped pacifier shapes tend to work well.

All the pacifiers of the present disclosure may be of different widths and/or heights. All the pacifiers of the present disclosure may have interchangeable parts. Finally, all the pacifiers of the present disclosure may be constructed by any manufacturing means.

Within this written description, the particular naming of the components, capitalization of terms, the attributes, data structures, or any other programming or structural aspect is not mandatory or significant, and the mechanisms that implement the present disclosure or its features may have different names, formats, or protocols. Further, the pacifier assembly may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

It should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

Having described the present disclosure above, various modifications of the techniques, procedures, material and equipment will be apparent to those in the art. It is intended that all such variations within the scope and spirit of the appended claims be embraced thereby.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

What is claimed is:

1. A pacifier assembly comprising:
 a nipple having a proximal portion and a distal portion, the distal portion configured to receive and analyze breath samples from a user via a breath analysis module; and
 a base portion attached to the proximal portion of the nipple, the base portion including a grip portion;
 wherein the breath analysis module is configured to analyze the breath samples by detecting and quantifying a select number of different molecules and/or organic compounds therefrom to derive nutritional information including nutrients pertaining to a diet of the user from the received breath samples in order to determine nutritional deficiencies of the user; wherein the base portion further includes one or more removable strips configured to display nutritional information values based on the breath samples received from the user via the nipple.

2. The pacifier assembly according to claim 1, wherein the nutritional information includes at least one of carbohydrates, fats, minerals, protein, fiber, vitamins, water, salt, sugar, sodium, antioxidants, and phytochemicals.

3. The pacifier assembly according to claim 1, wherein the breath samples are collected continuously and in real-time.

4. The pacifier assembly according to claim 1, wherein the nipple includes one or more sensors positioned thereon or embedded therein.

5. The pacifier assembly according to claim 4, wherein the one or more sensors measure at least one of pressure, humidity, temperature, oxygen levels, oxygen inhaled, oxygen exhaled, and carbon dioxide consumed.

6. The pacifier assembly according to claim 5, wherein the one or more sensors are configured to compute at least one of: (i) a difference between the oxygen inhaled and the oxygen exhaled, (ii) the oxygen levels of each of the breath samples received from the user via the nipple, and (iii) a respiratory quotient.

7. The pacifier assembly according to claim 1, wherein the one or more removable strips include a plurality of areas each configured to indicate different nutritional information values.

8. The pacifier assembly according to claim 7, wherein the nutritional information values are indicated via different indicia, colors or patterns.

9. The pacifier assembly according to claim 1, wherein the nutritional information is wirelessly transmitted to an electronic device.

10. The pacifier assembly according to claim 1, wherein at least one chemical breath profile is created based on the number of different molecules and/or organic compounds detected and quantified.

11. The pacifier assembly according to claim 1, wherein the number of different molecules and/or organic compounds are selected by a processor based on common molecules and/or common organic compounds associated with the nutritional information.

12. The pacifier assembly according to claim 1, wherein the breath analysis module is configured to trigger a display of the nutritional information on one or more portions of the pacifier assembly.

13. The pacifier assembly according to claim 1, farther comprising a processing unit configured to process historical data associated with the breath samples received from the user and creating a user breath profile.

14. The pacifier assembly according to claim 1, wherein the nipple is a hollow structure configured for receiving, storing, and analyzing saliva in conjunction with the breath samples of the user for providing the nutritional information.

15. A pacifier comprising:
a nipple having a breath analysis module configured to analyze one or more breath samples by detecting a select number of different molecules and/or organic compounds therefrom to derive nutritional information including nutrients pertaining to a diet of a user in order to determine nutritional deficiencies of the user; and
a base portion attached to the nipple, the base portion including a grip portion and one or more removable strips configured to display nutritional information values based on the one more breath samples received from the user via the nipple;
wherein at least one chemical breath profile is created based on the number of different molecules and/or organic compounds detected.

16. The pacifier according to claim 15, wherein the number of different molecules and/or organic compounds are selected by a processor based on relationships established between the nutritional information and trigger conditions.

17. The pacifier according to claim 16, wherein the trigger conditions are one or more of the following: hunger, thirst, dehydration, overfeeding, underfeeding, and lack of nutrients.

18. The pacifier according to claim 15, wherein the breath analysis module is configured to trigger a display of the nutritional information on one or more portions of the pacifier.

19. The pacifier according to claim 15, wherein, the breath analysis module is pre-programmed by a processor for selection of the number of different molecules and/or organic compounds for creating the at least one chemical breath profile, including the use of a combination of common and uncommon molecules and/or organic compounds.

* * * * *